(12) United States Patent
Nagasaki et al.

(10) Patent No.: US 10,244,763 B2
(45) Date of Patent: Apr. 2, 2019

(54) ANTIBACTERIAL LAYER-ATTACHED BASE MATERIAL, ANTIBACTERIAL SHEET, RADIATION PHOTOGRAPHING DEVICE, AND TOUCH PANEL

(71) Applicant: FUJIFILM Corporation, Tokyo (JP)

(72) Inventors: Hideo Nagasaki, Kanagawa (JP);
Michihiro Shibata, Kanagawa (JP);
Fumito Nariyuki, Kanagawa (JP);
Setsuko Shiratsuchi, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 15/277,724

(22) Filed: Sep. 27, 2016

(65) Prior Publication Data

US 2017/0013842 A1    Jan. 19, 2017

Related U.S. Application Data

(63) Continuation of application No. PCT/JP2015/059464, filed on Mar. 26, 2015.

(30) Foreign Application Priority Data

Mar. 28, 2014   (JP) ................. 2014-070044

(51) Int. Cl.
*A01N 25/10* (2006.01)
*A01N 25/34* (2006.01)
*A01N 59/16* (2006.01)
*B32B 27/06* (2006.01)
*B32B 27/18* (2006.01)
*G06F 3/041* (2006.01)

(52) U.S. Cl.
CPC ............ *A01N 59/16* (2013.01); *A01N 25/10* (2013.01); *B32B 27/06* (2013.01); *B32B 27/18* (2013.01); *G06F 3/041* (2013.01); *B32B 2307/7145* (2013.01); *B32B 2307/728* (2013.01); *B32B 2457/208* (2013.01); *G06F 2203/04103* (2013.01)

(58) Field of Classification Search
None
See application file for complete search history.

(56) References Cited

U.S. PATENT DOCUMENTS

| | | | |
|---|---|---|---|
| 6,013,372 A | 1/2000 | Hayakawa et al. | |
| 2005/0159503 A1* | 7/2005 | Kim .................. | C09D 5/033 523/122 |
| 2012/0034435 A1* | 2/2012 | Borrelli .............. | C03C 17/30 428/210 |
| 2014/0017335 A1 | 1/2014 | Dimov et al. | |
| 2014/0072783 A1 | 3/2014 | Borrelli et al. | |
| 2015/0118276 A1 | 4/2015 | Borrelli et al. | |
| 2015/0190550 A1* | 7/2015 | Nusko ................ | A01N 59/16 424/409 |

FOREIGN PATENT DOCUMENTS

| | | | | |
|---|---|---|---|---|
| CN | 103068764 A | 4/2013 | | |
| CN | 103347944 A | 10/2013 | | |
| JP | 10-305091 A | 11/1998 | | |
| JP | 2002-179514 A | 6/2002 | | |
| JP | 2002-337277 A | 11/2002 | | |
| JP | 2002337277 A | * 11/2002 | | |
| JP | 2005-226029 A | 8/2005 | | |
| JP | 2008-213206 A | 9/2008 | | |
| JP | 2009-167097 A | 7/2009 | | |
| JP | 2011-133800 A | 7/2011 | | |
| JP | 2013-010892 A | 1/2013 | | |
| JP | 2013-203935 A | 10/2013 | | |
| WO | WO-2012084072 A1 | * 6/2012 | ......... | A61L 24/0015 |
| WO | 2012/107435 A1 | 8/2012 | | |

OTHER PUBLICATIONS

English Translation of Hatakeyama et al. (JP 2002337277 A). Originally published in Japanese on Nov. 27, 2002. English translation obtained Oct. 31, 2017 from https://patents.google.com/patent/JP2002337277A/en#citedBy. 14 printed pages. (Year: 2002).*
Notification of Reasons for Refusal, dated Oct. 4, 2016, issued in corresponding JP Application No. 2014-070044, 6 pages in English and Japanese.
International Preliminary Report on Patentabililty and Written Opinion, dated Oct. 13, 2016, in International Application No. PCT/JP2015/059464, 7 pages in English.
International Search Report for PCT/JP2015/059464 dated Jun. 30, 2015.
Written Opinion for PCT/JP2015/059464 dated Jun. 30, 2015.
Communication dated Apr. 19, 2017, from the State Intellectual Property Office of the P.R.C., in counterpart Chinese application No. 201580016825.5.
Communication dated Feb. 10, 2017, from the European Patent Office in counterpart European Application No. 15768620.5.

* cited by examiner

*Primary Examiner* — Isaac Shomer
(74) *Attorney, Agent, or Firm* — Sughrue Mion, PLLC

(57) ABSTRACT

The present invention provides an antibacterial layer-attached base material which has excellent light resistance and includes an antibacterial layer exhibiting an antibacterial action within a short period of time, an antibacterial sheet, a radiation photographing device, and a touch panel. The antibacterial layer-attached base material of the present invention is an antibacterial layer-attached base material including: a base material; and an antibacterial layer which is disposed on at least a part of the surface of the base material, in which the antibacterial layer contains at least one antibacterial agent containing silver, and the amount of silver ions per a unit area measured in an extraction test is 15 to 50 ng/cm$^2$.

14 Claims, 1 Drawing Sheet

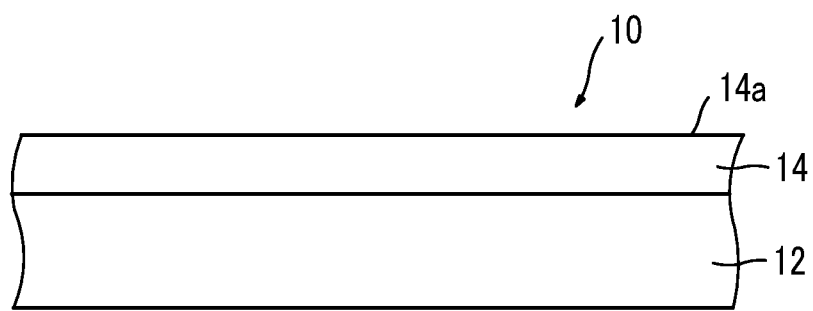

ANTIBACTERIAL LAYER-ATTACHED BASE MATERIAL, ANTIBACTERIAL SHEET, RADIATION PHOTOGRAPHING DEVICE, AND TOUCH PANEL

CROSS-REFERENCE TO RELATED APPLICATIONS

This application is a Continuation of PCT International Application No. PCT/JP2015/059464 filed on Mar. 26, 2015, which claims priority under 35 U.S.C. § 119(a) to Japanese Patent Application No. 2014-070044 filed on Mar. 28, 2014. The above application is hereby expressly incorporated by reference, in its entirety, into the present application.

BACKGROUND OF THE INVENTION

1. Field of the Invention

The present invention relates to an antibacterial layer-attached base material, an antibacterial sheet, a radiation photographing device, and a touch panel.

2. Description of the Related Art

In many cases, processing is performed on the surfaces of various products and members in accordance with the purpose to provide various functions. Among these, in recent years, technology of providing an antibacterial layer on the surface of a base material has been attracting attention.

For example, in many cases, a medical device used in a medical field continuously comes into contact with a plurality of patients. In addition, the surface of a touch panel is directly touched by a finger of an unspecified large number of operators. Therefore, there is a concern that a person may be infected with a disease if bacteria or the like are propagated on the surface thereof. It is possible to reduce a risk of propagation of bacteria or infection with a disease by providing an antibacterial layer on the surfaces of various devices such as a medical device or a touch panel.

As an example of such technology, a front plate consisting of a base material and a scratch-resistant film including an antibacterial agent which contains silver and consists of phosphate double salts is disclosed in JP2002-337277A.

SUMMARY OF THE INVENTION

In contrast, in recent years, in order to further increase the usage frequency of various devices (for example, medical device or touch panel), it has become necessary for an antibacterial action to be exhibited within a shorter period of time.

In addition, a base material having an antibacterial layer is exposed to illumination light or light from outside for a long period of time. At that time, it is necessary to prevent discoloration of the antibacterial layer. For example, if the antibacterial layer on the surface of a touch panel is discolored, there is a concern that the visibility of the touch panel may be impaired.

That is, it is necessary for the antibacterial layer to have excellent light resistance and to exhibit an antibacterial action within a short period of time.

The present inventors have conducted studies on the antibacterial layer-attached base material disclosed in JP2002-337277A. As a result, it is necessary to further improve the antibacterial layer-attached base material since the antibacterial layer-attached base material does not satisfy the above-described requirements.

The present invention has been made in consideration of the above-described circumstances, and an object of the present invention is to provide an antibacterial layer-attached base material which has excellent light resistance and includes an antibacterial layer exhibiting an antibacterial action within a short period of time.

In addition, another object of the present invention is to provide an antibacterial sheet, and a radiation photographing device and a touch panel which include the above-described antibacterial layer-attached base material.

The present inventors have conducted extensive studies on the above-described problems. As a result, they have found that it is possible to solve the above-described problems using the following configuration.

(1) An antibacterial layer-attached base material comprising:

a base material; and an antibacterial layer which is disposed on at least a part of the surface of the base material, in which the antibacterial layer contains at least one antibacterial agent containing silver, and in which the amount of silver ions per a unit area measured in an extraction test to be described below is 15 to 50 ng/cm$^2$.

(2) The antibacterial layer-attached base material according to (1), in which the water contact angle of the surface of the antibacterial layer is less than or equal to 40°.

(3) The antibacterial layer-attached base material according to (1) or (2), in which the antibacterial agent is a silver-supporting carrier containing a carrier and silver which is supported on the carrier.

(4) The antibacterial layer-attached base material according to any one of (1) to (3), in which the antibacterial layer contains a polymer having a hydrophilic group.

(5) The antibacterial layer-attached base material according to (4), in which the hydrophilic group contains a polyoxyalkylene group.

(6) The antibacterial layer-attached base material according to any one of (1) to (4), in which the antibacterial layer is formed by subjecting a monomer having a hydrophilic group, and a curable composition having at least an antibacterial agent containing silver to a curing treatment.

(7) The antibacterial layer-attached base material according to (6), in which the hydrophilic group in the monomer which has a hydrophilic group contains a polyoxyalkylene group.

(8) A radiation photographing device comprising:

the antibacterial layer-attached base material according to any one of (1) to (7) on the surface thereof.

(9) A touch panel comprising:

the antibacterial layer-attached base material according to any one of (1) to (7) on the surface thereof.

(10) An antibacterial sheet comprising:

an antibacterial agent, in which the antibacterial agent contains at least one antibacterial agent containing silver, and in which the amount of silver ions per a unit area measured in an extraction test to be described below is 15 to 50 ng/cm$^2$.

(11) The antibacterial sheet according to (10), in which the water contact angle of the surface of the antibacterial sheet is less than or equal to 40°.

(12) The antibacterial sheet according to (10) or (11),
in which the antibacterial agent is a silver-supporting carrier containing a carrier and silver which is supported on the carrier.

(13) The antibacterial sheet according to any one of (10) to (12), further comprising:
a polymer having a hydrophilic group.

(14) The antibacterial sheet according to (13),
in which the hydrophilic group contains a polyoxyalkylene group.

(15) The antibacterial sheet according to any one of (10) to (14), which is formed by subjecting a monomer having a hydrophilic group, and a curable composition having at least an antibacterial agent containing silver to a curing treatment.

(16) The antibacterial sheet according to (15),
in which the hydrophilic group in the monomer which has a hydrophilic group contains a polyoxyalkylene group.

According to the present invention, it is possible to provide an antibacterial layer-attached base material which has excellent light resistance and includes an antibacterial layer exhibiting an antibacterial action within a short period of time.

In addition, according to the present invention, it is also possible to provide an antibacterial sheet, and a radiation photographing device and a touch panel which include the above-described antibacterial layer-attached base material.

BRIEF DESCRIPTION OF THE DRAWINGS

FIG. 1 is a cross-sectional view of an embodiment of an antibacterial layer-attached base material of the present invention.

DESCRIPTION OF THE PREFERRED EMBODIMENTS

Hereinafter, an antibacterial layer-attached base material, an antibacterial sheet, a radiation photographing device, and a touch panel of the present invention will be described.

In the present specification, the numerical range represented by "to" means a range including numerical values denoted before and after "to" as a lower limit value and an upper limit value.

Examples of a characteristic point of the present invention include controlling the amount of silver ions eluted from an antibacterial layer. Specifically, it has been found that, if the amount of silver ions eluted (extracted) from the antibacterial layer in a predetermined extraction liquid used in an extraction test to be described below is greater than or equal to a predetermined value, it is possible to obtain an antibacterial action within a shorter period of time. In addition, it has been found that, if the elution (extraction) amount thereof is less than or equal to a predetermined value, the present invention has excellent light resistance.

Hereinafter, first, the antibacterial layer-attached base material of the present invention will be described in detail.

FIG. 1 is a cross-sectional view of an embodiment of the antibacterial layer-attached base material of the present invention. As shown in FIG. 1, an antibacterial layer-attached base material 10 has a base material 12 and an antibacterial layer 14 which is disposed on the base material 12. The antibacterial layer 14 may be disposed on at least a part of the surface of the base material 12.

Hereinafter, each member will be described in detail.
<Base Material>
The base material plays a role of supporting an antibacterial layer, and the type of base material is not particularly limited. In addition, the base material may constitute a part (for example, a front plate) of various devices as will be described below.

The shape of the base material is not particularly limited, but examples thereof include a plate shape, a film shape, a sheet shape, a tube shape, a fiber shape, and a particle shape. In addition, the surface of the base material on which an antibacterial layer to be described below is disposed may be a flat surface, a concave surface, or a convex surface.

The material constituting the base material is not particularly limited, and examples thereof include metal, glass, ceramic, and plastic (resin). Among these, plastic is preferable from the viewpoint of handling properties. In other words, a resin base material is preferable.

<Antibacterial Layer>
The antibacterial layer is a layer which is disposed on at least a part of the surface of a base material and has an antibacterial action.

The antibacterial layer contains at least one antibacterial agent containing silver.

Silver (silver atom) may be contained in the antibacterial agent (hereinafter, also referred to as a silver-based antibacterial agent) which contains silver, and the type thereof is not particularly limited. In addition, the form of silver is also not particularly limited. For example, silver is contained in a form of metal silver, silver ions, or silver salts (including silver complexes). In the present specification, the silver complexes are included in a range of silver salts.

Examples of the silver salts include silver acetate, silver acetylacetonate, silver azide, silver acetylide, silver arsenite, silver benzoate, silver hydrogen fluoride, silver bromate, silver bromide, silver carbonate, silver chloride, silver chlorate, silver chromate, silver citrate, silver cyanate, silver cyanide, silver (cis,cis-1,5-cyclooctadiene)-1,1,1,5,5,5-hexafluoroacetylacetonate, silver diethyldithiocarbamate, silver (I) fluoride, silver (II) fluoride, silver 7,7-dimethyl-1,1,1,2,2,3,3-heptafluoro-4,6-octanedionate, silver hexafluoroantimonate, silver hexafluoroarsenate, silver hexafluorophosphate, silver iodate, silver iodide, silver isothiocyanate, silver potassium cyanide, silver lactate, silver molybdate, silver nitrate, silver nitrite, silver (I) oxide, silver (II) oxide, silver oxalate, silver perchlorate, silver perfluorobutyrate, silver perfluoropropionate, silver permanganate, silver perrhenate, silver phosphate, silver picrate monohydrate, silver propionate, silver selenate, silver selenide, silver selenite, silver sulfadiazine, silver sulfate, silver sulfide, silver sulfite, silver telluride, silver tetrafluoroborate, silver tetraiodinecurate, silver tetratungstate, silver thiocyanate, silver p-toluene sulfonate, silver trifluoromethanesulfonate, silver trifluoroacetate, and silver vanadate.

Examples of the silver complexes include a histidine silver complex, a methionine silver complex, a cysteine silver complex, a silver aspartate complex, a silver pyrrolidone carboxylate complex, a silver oxotetrahydrofuran carboxylate complex, or an imidazole silver complex.

Examples of the silver-based antibacterial agent include an organic antibacterial agent such as the above-described silver salts (silver complexes) and an inorganic antibacterial agent containing a carrier to be described below. However, the types thereof are not particularly limited.

Among the silver-based antibacterial agents, a silver-supporting carrier containing a carrier and silver which is supported on the carrier is preferable from the viewpoint of more excellent light resistance of an antibacterial layer and/or more excellent antibacterial properties (hereinafter, also referred to that the "viewpoint of more excellent effect of the present invention").

The type of carrier is not particularly limited, and examples thereof include zinc calcium phosphate, calcium phosphate, zirconium phosphate, aluminum phosphate, calcium silicate, activated carbon, activated alumina, silica gel, zeolite, hydroxyapatite, zirconium phosphate, titanium phosphate, potassium titanate, hydrous bismuth oxide, hydrous zirconium oxide, and hydrotalcite. Examples of the zeolite include natural zeolite such as chabazite, mordenite, erionite, and clinoptilolite, and synthetic zeolite such as A-type zeolite, X-type zeolite, and Y-type zeolite.

In addition, so-called ceramics are preferable as the carriers from the viewpoint of more excellent effect of the present invention.

The average particle diameter of the above-described silver-supporting carrier is not particularly limited, but is preferably 0.1 to 10 μm and more preferably 0.1 to 2 μm from the viewpoint of more excellent effect of the present invention. The above-described average particle diameter is a value which is obtained by measuring the diameters of at least 10 arbitrary silver-supporting carriers using a microscope and arithmetically averaging the measured diameters.

The content of silver in a silver-based antibacterial agent is not particularly limited. For example, in a case of the above-described silver-supporting carrier, the content of silver is preferably 0.1 to 10 mass % and more preferably 0.3 to 5 mass % with respect to the total mass of the silver-supporting carrier.

The content of the above-described silver-based antibacterial agent in an antibacterial layer is not particularly limited. However, it is preferable that the silver-based antibacterial agent is contained in the antibacterial layer such that the content of silver with respect to the total mass of the antibacterial layer becomes 0.001 to 20 mass % (preferably 0.001 to 5 mass %) from the viewpoint of more excellent effect of the present invention.

In addition, in a case of using an organic antibacterial agent as the silver-based antibacterial agent, the content of the antibacterial agent is not particularly limited, but is preferably 1 to 4 mass % with respect to the total mass of the antibacterial layer from the viewpoints that the mechanical strength of the antibacterial layer becomes more excellent and the effect of the present invention becomes more excellent.

Furthermore, in a case of using an inorganic antibacterial agent as the silver-based antibacterial agent, the content of the antibacterial agent is not particularly limited, but is preferably 0.001 to 10 mass % and more preferably 0.01 to 5 mass % with respect to the total mass of the antibacterial layer from the viewpoints that the mechanical strength of the antibacterial layer becomes more excellent and the effect of the present invention becomes more excellent.

Components other than the above-described silver-based antibacterial agent may be contained in the antibacterial layer.

For example, a polymer (hereinafter, also simply referred to as a "hydrophilic polymer") which has a hydrophilic group may be contained in the antibacterial layer. By making the antibacterial layer contain the hydrophilic polymer, the antibacterial layer exhibits more hydrophilicity, and therefore, it is possible to more easily remove contaminants adhered to the top of the antibacterial layer through cleaning using water or the like.

The type of hydrophilic group is not particularly limited, and examples thereof include a polyoxyalkylene group (for example, a polyoxyethylene group, a polyoxypropylene group, or a polyoxyalkylene group in which an oxyethylene group and an oxypropylene group are blocked or to which the oxyethylene group and an oxypropylene group are randomly bonded), an amino group, a carboxyl group, an alkali metal salt of a carboxyl group, a hydroxy group, an alkoxy group, an amide group, a carbamoyl group, a sulfonamide group, a sulfamoyl group, a sulfonic acid group, and an alkali metal salt of a sulfonic acid group. Among these, a polyoxyalkylene group is preferable from the viewpoint of more excellent effect of the present invention.

The structure of a main chain of the hydrophilic polymer is not particularly limited, and examples thereof include polyurethane, poly(meth)acrylate, polystyrene, polyester, polyamide, polyimide, and polyurea.

The poly(meth)acrylate has a concept including both polyacrylate and polymethacrylate.

As an example of a suitable aspect of the hydrophilic polymer, there is a polymer obtained by polymerizing a monomer (hereinafter, also simply referred to as a "hydrophilic monomer") which has the above-described hydrophilic group.

The hydrophilic monomer means a compound having the above-described hydrophilic group and a polymerizable group. The definition of the hydrophilic group is as described above.

The number of hydrophilic groups in a hydrophilic monomer is not particularly limited, but is preferably greater than or equal to two, more preferably two to six, and still more preferably two to three from the viewpoint that an antibacterial layer exhibits more hydrophilicity.

The type of polymerizable group is not particularly limited, and examples thereof include a radical polymerizable group, a cationic polymerizable group, and anionic polymerizable group. Examples of the radical polymerizable group include a (meth)acryloyl group, an acrylamide group, a vinyl group, a styryl group, and an allyl group. Examples of the cationic polymerizable group include a vinyl ether group, an oxiranyl group, and an oxetanyl group. Among these, a (meth)acryloyl group is preferable.

The (meth)acryloyl group has a concept including both acryloyl group and a methacryloyl group.

The number of polymerizable groups in a hydrophilic monomer is not particularly limited, but is preferably greater than or equal to two, more preferably two to six, and still more preferably two to three from the viewpoint of more excellent mechanical strength of an antibacterial layer which can be obtained.

As an example of a suitable aspect of the hydrophilic monomer, there is a compound represented by the following Formula (1).

Formula (1)

In Formula (1), $R_1$ represents a substituent. The type of substituent is not particularly limited, and examples thereof include a well-known substituent. For example, there is a hydrocarbon group (for example, an alkyl group or aryl group) which may have a hetero atom or the above-described hydrophilic group.

$R_2$ represents a polymerizable group. The definition of the polymerizable group is as described above.

$L_1$ represents a single bond or a divalent linking group. The type of divalent linking group is not particularly limited, and examples thereof include —O—, —CO—, —NH—, —CO—NH—, —COO—, —O—COO—, an alkylene group, an arylene group, a heteroaryl group, and a combination thereof.

L$_2$ represents a polyoxyalkylene group. The polyoxyalkylene group means a group represented by the following Formula (2).

*—(OR$_3$)$_m$—*  Formula (2)

In Formula (2), R$_3$ represents an alkylene group (for example, an ethylene group or a propylene group). m represents an integer of 2 or more, preferably 2 to 10, and more preferably 2 to 6. * represents a bonding position.

n represents an integer of 1 to 4.

Specific examples of the hydrophilic monomer include polyoxyalkylene-modified pentaerythritol triacrylate, and polyoxyalkylene-modified bisphenol A diacrylate.

When obtaining a hydrophilic polymer, the above-described hydrophilic monomer and another monomer (a monomer containing no hydrophilic group) may be used together. That is, a hydrophilic polymer which can be obtained by copolymerizing the hydrophilic monomer and the other monomer (a monomer other than the hydrophilic monomer) may be used.

The type of the other monomer is not particularly limited, and any well-known monomers having a polymerizable group can be appropriately used. The definition of the polymerizable group is as described above.

Among these, a polyfunctional monomer having two or more polymerizable groups is preferable from the viewpoint of more excellent the mechanical strength of an antibacterial layer. The polyfunctional monomer acts as a so-called crosslinking agent.

The number of polymerizable groups contained in a polyfunctional monomer is not particularly limited, but is preferably two to ten and more preferably two to six from the viewpoint of more excellent the mechanical strength of an antibacterial layer and handling properties.

Examples of the polyfunctional monomer include trimethylolpropane triacrylate, tetramethylolmethane tetraacrylate, dipentaerythritol hexaacrylate, and pentaerythritol tetraacrylate.

The mixing ratio (mass of a hydrophilic monomer/mass of another monomer) of a hydrophilic monomer and another monomer (particularly, a polyfunctional monomer) is not particularly limited, but is preferably 0.01 to 10 and more preferably 0.1 to 10 from the viewpoint of easy controlling of hydrophilicity of an antibacterial layer.

The content of the above-described hydrophilic polymer in an antibacterial layer is not particularly limited, but is preferably greater than or equal to 50 mass %, more preferably greater than or equal to 70 mass %, and still more preferably greater than or equal to 90 mass % with respect to the total mass of the antibacterial layer from the viewpoint of more excellent removing properties due to cleaning of contaminants on the antibacterial layer.

(Method for Producing Antibacterial Layer)

The method for producing an antibacterial layer is not particularly limited, and a well-known method can be employed. Examples thereof include a method for forming an antibacterial layer by coating the top of a base material with a composition containing the above-described silver-based antibacterial agent, or a method for pasting an antibacterial sheet containing a silver-based antibacterial agent, which has been separately prepared, to the base material at a predetermined position.

Among these, a method (coating method) for forming a coating film by coating a base material with the above-described composition (curable composition) containing a hydrophilic monomer and a silver-based antibacterial agent at a predetermined position and subjecting the coating film to a curing treatment to form an antibacterial layer is preferable from the viewpoint of easier adjustment of the thickness of the antibacterial layer or surface unevenness.

The composition contains, for example, above-described hydrophilic monomer and silver-based antibacterial agent, but may contain other components (the above-described another monomer, a lubricant, a solvent (water or an organic solvent)).

The composition may contain a polymerization initiator. By making the composition contain a polymerization initiator, polymerization more efficiently progresses in a coating film, thereby forming an antibacterial layer excellent in the mechanical strength. The type of polymerization initiator is not particularly limited, and an optimum kind of polymerization initiator is selected through the curing treatment method. For example, a thermopolymerization initiator or a photopolymerization initiator is selected. More specific examples thereof include aromatic ketones such as benzophenone or phenylphosphine oxide, α-hydroxyalkylphenone-based compound (BASF IRGACURE 184, 127, 2959, DAROCUR 1173, or the like), and phenylphosphine oxide-based compound (MAPO: BASF LUCIRIN TPO, BAPO: BASF IRGACURE 819).

The content of the polymerization initiator contained in a composition is not particularly limited, but is preferably 0.1 to 15 parts by mass and more preferably 1 to 6 parts by mass with respect to 100 parts by mass of the total mass of the hydrophilic monomer and the other monomer.

The method for coating with a composition is not particularly limited, and a well-known coating method is employed.

In addition, the curing treatment method is not particularly limited, and examples thereof include a heating treatment or a light irradiation treatment.

(Characteristics of Antibacterial Layer)

The average thickness of an antibacterial layer is not particularly limited, but is preferably 0.5 to 20 μm and more preferably 1 to 10 μm from the viewpoints of mechanical characteristics and antibacterial properties.

As a method for measuring the average thickness of an antibacterial layer, the average thickness of an antibacterial layer is measured by embedding a sample piece of the antibacterial layer in a resin, cutting a cross section a microtome, and observing the cut cross section using a scanning electron microscope. The thicknesses of the antibacterial layer at arbitrary 10 positions are measured and are arithmetically averaged.

The water contact angle of the surface of an antibacterial layer is not particularly limited, but is preferably less than or equal to 40°, more preferably less than or equal to 30°, and still more preferably less than or equal to 25° from the viewpoints of more excellent removing properties of contaminants on the antibacterial layer due to cleaning and more excellent antibacterial properties. The lower limit thereof is not particularly limited, but there are many cases where the water contact angle is greater than or equal to 5° from the viewpoint of characteristics of materials to be used.

In the present specification, the water contact angle is measured based on a still liquid drop method of JIS R3257: 1999. LSE-ME1 (software: 2WIN MINI) manufactured by NIC is used for the measurement. More specifically, 2 μl of liquid droplets of pure water is added dropwise to the surface of an antibacterial layer at 20° C. of room temperature while keeping a horizontal posture, and the contact angle is measured at a time point of 20 seconds after the dropwise addition.

<Antibacterial Layer-Attached Base Material>

In the above-described antibacterial layer-attached base material including a base material and an antibacterial layer, the amount of silver ions per a unit area measured in an extraction test to be described below shows 15 to 50 ng/cm$^2$, and is preferably 15 to 40 ng/cm$^2$ and more preferably 15 to 30 ng/cm$^2$ from the viewpoint of more excellent effect of the present invention.

In a case where the above-described amount of silver ions is less than 15 ng/cm$^2$, the antibacterial layer-attached base material is inferior in antibacterial properties. In a case where the amount of silver ions is greater than 50 ng/cm$^2$, the antibacterial layer-attached base material is inferior in light resistance.

Hereinafter, the method of the extraction test will be described in detail.

In the extraction test, a 1/500 common broth medium defined in JIS Z 2801:2010 is used as an extraction liquid. The temperature of the extraction liquid is controlled so as to be at 35±1° C., and an antibacterial layer (in example 1, the area of the antibacterial layer is 4 cm$^2$ (2 cm×2 cm)) in an antibacterial layer-attached base material is brought into contact with the extraction liquid (in the case of the above-described example 1, the amount of liquid is 9 mL) for an hour. As the method for bringing the antibacterial layer into contact with the extraction liquid, a method for immersing the antibacterial layer-attached base material in the extraction liquid is carried out.

Next, the antibacterial layer-attached base material is collected from the extraction liquid after the completion of the contact performed for an hour, and the amount (ng) of silver ions extracted in the extraction liquid is measured. The measurement of the amount of silver ions in the extraction liquid is carried out through atomic absorption spectrometry (CONTRAA700 manufactured by Analytic Jena AG), and the amount of silver ions is obtained using a calibration curve which has been previously prepared.

When measuring the amount of silver ions, it is preferable to add nitric acid (about 1 mL) to the extraction liquid in order to improve stability of the measurement as necessary.

Next, the obtained amount of silver ions is divided by the contact area (in the case of the above-described example 1, 4 cm$^2$) between the antibacterial layer and the extraction liquid to calculate the amount of silver ions per a unit area (ng/cm$^2$). The contact area between the antibacterial layer and the extraction liquid means an area in which the surface of the antibacterial layer comes into contact with the extraction liquid when the antibacterial layer is brought into contact with the extraction liquid. The contact area means, for example, an area of a main surface 14a on a side opposite to the base material 12 side of the antibacterial layer 14 in FIG. 1.

The obtained amount of silver ions represents the degree of elution (extraction) of silver ions from the antibacterial layer.

The above-described antibacterial layer-attached base material can be applied to various applications, and can be disposed on the surface of various devices. In the device on which this antibacterial layer-attached base material is disposed on the surface, it is possible to obtain antibacterial properties within a short period of time and excellent light resistance.

Examples of the device to which the antibacterial layer-attached base material is applied include a radiation photographing device and a touch panel. In a case where the antibacterial layer-attached base material is applied to these devices, a part (front plate) of various devices which supports the antibacterial layer may correspond to the base material.

The above-described antibacterial layer itself can be used as an antibacterial sheet. The configuration of the antibacterial sheet is the same as that of the above-described antibacterial layer, and the above-described extraction test is also carried out using the antibacterial sheet instead of using the antibacterial layer. That is, the amount of silver ions per a unit area, which has been obtained by bringing the predetermined extraction liquid described above into contact with the antibacterial sheet, measuring the amount of silver ions extracted in the extraction liquid, and dividing the obtained value by the contact area between the antibacterial sheet and the extraction liquid, may be within the predetermined range described above.

EXAMPLES

Hereinafter, the present invention will be described in more detail using Examples, but is not limited thereto.

(Preparation of Curable Composition)

A curable composition was prepared by mixing components shown below.

Hydrophilic monomer: Miramer M4004 (manufactured by Toyo Chemicals Co., Ltd.) 76 parts by mass Cross-linking agent: A-DPH (manufactured by SHIN-NAKAMURA CHEMICAL CO., LTD.) 21 parts by mass Polymerization initiator: IRGACURE (manufactured by BASF SE) 3 parts by mass Solvent component (1): methyl alcohol 15 parts by mass Solvent component (2): propylene glycol monomethyl ether 35 parts by mass Examples and Comparative Examples A silver ceramic particle dispersion liquid (manufactured by Fuji Chemical Industries, Ltd., average particle diameter of 0.8 μm) was added to and mixed with the curable composition prepared in the above according to the ratio shown in Table 1 to prepare a curable composition for forming an antibacterial layer.

A polycarbonate sheet (CARBOGLASS CFR110C manufactured by ASAHI GLASS CO., LTD.) was coated with the obtained curable composition for forming an antibacterial layer so as to obtain an antibacterial layer having a thickness shown in Table 1, the coated polycarbonate sheet was dried for 30 minutes at 60° C. Then, an evaluation sample (antibacterial layer-attached base material) was produced after forming an antibacterial layer by curing a monomer through UV irradiation.

In Example 6, the mass ratio of a hydrophilic monomer to a cross-linking agent was controlled so as to make the water contact angle be a predetermined value.

<Evaluation>

The following evaluation was performed using evaluation samples which have been obtained in Examples and Comparative Examples. The results are collectively shown in Table 1.

(Method for Evaluating Antibacterial Properties)

Evaluation of antibacterial properties was performed by carrying out a test after changing the contact time with a bacterial liquid from 24 hours to 1 hour in accordance with an evaluation method disclosed in JIS Z 2801:2010. The number (pieces/cm$^2$) of bacteria after each test was measured. The evaluation was performed in accordance with the following criteria. The type of *bacterium* was *Escherichia coli*. "A" and "B" are practically preferable.

"A": The number of bacteria is less than 5 pieces/cm$^2$

"B": the number of bacteria is greater than or equal to 5 pieces/cm$^2$ and less than 10 pieces/cm$^2$ "C": the number of bacteria is greater than or equal to 10 pieces/cm$^2$ (Light Resistance Test)

The discoloration of an antibacterial layer in an evaluation sample after irradiation performed using XENON WEATHER METER (manufactured by Suga Test Instruments Co., Ltd.) for 10 hours at an output of 60 W/m$^2$ was visually evaluated from the following viewpoints. "A" is practically preferable.

"A": There is no discoloration

"B": There is discoloration

In addition, the above-described extraction test was carried out using each of the evaluation samples obtained in Examples and Comparative Examples.

In addition, the water contact angle of an antibacterial layer in each of the evaluation samples obtained in Examples and Comparative Examples was measured through the above-described method. The results are shown in Table 1.

In Table 1, the expression "mass (mass %) of antibacterial agent" means the content (mass %) of an antibacterial agent with respect to the mass (the mass of the total solid content in a curable composition) of components of a cured material in an antibacterial layer.

In Table 1, the column "amount of Ag ions" means the amount of silver ions per a unit area measured in the extraction test.

TABLE 1

| | Antibacterial layer | | | | | |
|---|---|---|---|---|---|---|
| | Mass (mass %) of antibacterial agent | Film thickness (μm) | Amount of Ag ions (ng/cm$^2$) | Evaluation | | |
| | | | | Antibacterial properties | Light resistance | Water contact angle (°) |
| Example 1 | 0.5 | 4.0 | 15.8 | A | A | 25 |
| Example 2 | 0.7 | 4.0 | 19.1 | A | A | 20 |
| Example 3 | 1.0 | 4.0 | 23.2 | A | A | 22 |
| Example 4 | 1.5 | 4.0 | 25.0 | A | A | 23 |
| Example 5 | 2.0 | 5.0 | 40.0 | A | A | 25 |
| Example 6 | 1.5 | 4.0 | 20.2 | B | A | 50 |
| Comparative Example 1 | 0.5 | 3.1 | 12.5 | C | A | 30 |
| Comparative Example 2 | 0.5 | 2.0 | 6.3 | C | A | 23 |
| Comparative Example 3 | 3.0 | 5.0 | 63.2 | A | B | 21 |

As shown in Table 1, the antibacterial layer-attached base material of the present invention has excellent antibacterial properties within a short period of time and has also excellent light resistance.

In contrast, in Comparative Examples 1 and 2 in which the range of the amount of silver ions is smaller than a predetermined range, it is impossible to obtain predetermined antibacterial properties. In Comparative Example 3 in which the range of the amount of silver ions is larger than a predetermined range, the light resistance is deteriorated.

EXPLANATION OF REFERENCES

10: antibacterial layer-attached base material
12: base material
14: antibacterial layer

What is claimed is:

1. An antibacterial layer-attached base material comprising:
   a base material; and
   an antibacterial layer which is disposed on at least a part of the surface of the base material,
   wherein the antibacterial layer contains at least one antibacterial agent containing silver,
   wherein the amount of silver ions per a unit area measured in the following extraction test is 15.8 to 40 ng/cm$^2$,
   wherein, in the extraction test, the amount of silver ions per a unit area is obtained by using a 1/500 common broth medium defined in JIS Z 2801:2010 as an extraction liquid, controlling the temperature of the extraction liquid so as to be at 35±1° C., bringing the extraction liquid into contact with the antibacterial layer in the antibacterial layer-attached base material for an hour, measuring the amount of silver ions extracted in the extraction liquid, and dividing the obtained value by the contact area of the antibacterial layer with respect to the extraction liquid; the unit of the amount of silver ions is ng; the unit of the contact area is cm$^2$; and the unit of the amount of silver ions per a unit area is ng/cm$^2$,
   wherein the antibacterial layer is formed by subjecting a curable composition containing at least a monomer having a polyoxyalkylene group and a polymerizable group and the antibacterial agent to a curing treatment,
   wherein the mass percentage of the antibacterial agent with respect to the mass of the total solid content of components of the cured material in the antibacterial layer is between 0.5% and 2.0%,
   wherein the antibacterial layer in the form of a film with a thickness of 4.0 μm to 5.0 μm, and
   wherein the water contact angle is between 20° and 25°.

2. The antibacterial layer-attached base material according to claim 1,
   wherein the water contact angle of the surface of the antibacterial layer is less than or equal to 40°.

3. The antibacterial layer-attached base material according to claim 1,
   wherein the antibacterial agent is a silver-supporting carrier containing a carrier and silver which is supported on the carrier.

4. A radiation photographing device comprising:
   the antibacterial layer-attached base material according to claim 1 on the surface thereof.

5. A touch panel comprising:
   the antibacterial layer-attached base material according to claim 1 on the surface thereof.

6. The antibacterial layer-attached base material according to claim 1,
   wherein the antibacterial agent is an inorganic antibacterial agent containing a carrier.

7. The antibacterial layer-attached base material according to claim 1,
   wherein the antibacterial agent is a silver-supporting carrier containing a ceramics and silver which is supported on the ceramics.

8. The antibacterial layer-attached base material according to claim 1, wherein the content of the antibacterial agent is 0.001 to 10 mass % with respect to the total mass of the antibacterial layer.

9. An antibacterial sheet comprising:
an antibacterial agent,
wherein the antibacterial agent contains at least one antibacterial agent containing silver,
wherein the amount of silver ions per a unit area measured in the following extraction test is 15.8 to 40.0 ng/cm$^2$,
wherein, in the extraction test, the amount of silver ions per a unit area is obtained by using a 1/500 common broth medium defined in JIS Z 2801:2010 as an extraction liquid, controlling the temperature of the extraction liquid so as to be at 35±1° C., bringing the extraction liquid into contact with the antibacterial sheet for an hour, measuring the amount of silver ions extracted in the extraction liquid, and dividing the obtained value by the contact area of the antibacterial sheet with respect to the extraction liquid; the unit of the amount of silver ions is ng; the unit of the contact area is cm$^2$; and the unit of the amount of silver ions per a unit area is ng/cm$^2$,
wherein the antibacterial sheet is formed by subjecting a curable composition containing at least a monomer having a polyoxyalkylene group and a polymerizable group and the antibacterial agent to a curing treatment wherein the mass percentage of the antibacterial agent with respect to the mass of the total solid content of components of the cured material in the antibacterial layer is between 0.5% and 2.0%,
wherein the antibacterial layer in the form of a film with a thickness of 4.0 μm to 5.0 μm, and
wherein the water contact angle is between 20° and 25°.

10. The antibacterial sheet according to claim 9,
wherein the water contact angle of the surface of the antibacterial sheet is less than or equal to 400.

11. The antibacterial sheet according to claim 9,
wherein the antibacterial agent is a silver-supporting carrier containing a carrier and silver which is supported on the carrier.

12. The antibacterial sheet according to claim 9,
wherein the antibacterial agent is an inorganic antibacterial agent containing a carrier.

13. The antibacterial sheet according to claim 9,
wherein the antibacterial agent is a silver-supporting carrier containing a ceramics and silver which is supported on the ceramics.

14. The antibacterial sheet according to claim 9,
wherein the content of the antibacterial agent is 0.001 to 10 mass % with respect to the total mass of the antibacterial layer.

* * * * *